United States Patent
Kajitani et al.

(10) Patent No.: US 6,859,663 B2
(45) Date of Patent: Feb. 22, 2005

(54) MYOELECTRIC-PATTERN CLASSIFICATION METHOD AND APPARATUS

(75) Inventors: Isamu Kajitani, c/o National Institute of Advanced Industrial Science and Technology (AIST), AIST Tsukuba Center 2, 1-1-1 Umezono, Tsukuba-shi, Ibaraki, 305-8568 (JP); Tetsuya Higuchi, c/o National Institute of Advanced Industrial Science and Technology (AIST), AIST Tsukuba Center 2, 1-1-1 Umezono, Tsukuba-shi, Ibaraki, 305-8568 (JP)

(73) Assignees: National Institute of Advanced Industrial Science and Technology, Tokyo (JP); Isamu Kajitani, Tsukuba (JP); Tetsuya Higuchi, Tsukuba (JP)

( * ) Notice: Subject to any disclaimer, the term of this patent is extended or adjusted under 35 U.S.C. 154(b) by 584 days.

(21) Appl. No.: 10/057,900

(22) Filed: Jan. 29, 2002

(65) Prior Publication Data

US 2002/0191842 A1 Dec. 19, 2002

(30) Foreign Application Priority Data

Jan. 30, 2001 (JP) .................................. 2001-020880

(51) Int. Cl.$^7$ ................................. A61B 5/04
(52) U.S. Cl. ....................................... 600/546
(58) Field of Search .......................... 600/546; 623/24, 623/25, 57, 58, 63; 700/213, 250; 706/13, 14; 375/316

(56) References Cited

U.S. PATENT DOCUMENTS 5,376,128 A * 12/1994 Bozeman, Jr. ............... 623/24

OTHER PUBLICATIONS

I. Kajitani, et al., The Institute of Electronics Information and Communications Engineers, Technical Report of IEICE, PRMU98–85, pp. 9–16, "Developing Adaptable EMG Controlled Prostheses to Disabled People", Sep. 1998 ( with English Abstract).

* cited by examiner

Primary Examiner—Eric F. Winakur
Assistant Examiner—Brian Szmal
(74) Attorney, Agent, or Firm—Oblon, Spivak, McClelland, Maier & Neustadt, P.C.

(57) ABSTRACT

A myoelectric pattern that is an action potential generated by a coordinated action of a plurality of muscles is measured by a group of surface electrodes on a skin surface, and a feature pattern is extracted from the measured myoelectric pattern. Redundant coding is used to encode the extracted feature pattern into a bit pattern, the coded bit pattern is subjected to pattern classification, and output control signal is generated.

2 Claims, 6 Drawing Sheets

The muscle contraction scheme

An example of sampled myoelectric signals

An example of the rectified myoelectric signals

MYOELECTRIC-PATTERN CLASSIFICATION METHOD AND APPARATUS

BACKGROUND OF THE INVENTION

1. Field of the Invention

The present invention relates to a myoelectric-pattern classification method and apparatus in a method of interfacing muscle action potential (myoelectric pattern).

2. Description of the Prior Art

FIG. 2 is a drawing used to illustrate a prior-art apparatus that manipulates a target by extracting a feature value from a myoelectric pattern, encoding it into a bit string and classifying the encoded bit pattern. In the drawing, ① denotes myoelectric patterns, ② a surface electrode group, ③ amplification and smoothing apparatuses, ④ a feature-pattern extraction apparatus, ⑤ an encoder (binary code/gray code), ⑥ a pattern classifier, and ⑦ a control target such as a motor, a robot, a device for the disabled, rehabilitation device, a myoelectric arm prosthesis, a game, and so forth.

As shown in the drawing, a myoelectric pattern ① that is an action potential generated by the coordinated action of a plurality of muscles, is measured by one or a plurality of surface electrode groups ② on a skin surface. What is measured is the sum of the action potentials generated by the plurality of muscles. Next, the sum potential obtained is subjected to amplification and smoothing by the amplification and smoothing apparatuses ③. The feature-pattern extraction apparatus ④ extracts a feature pattern from the amplified, smoothed signal. The encoder ⑤ encodes the obtained feature pattern into a binary-code or gray-code bit-string. The pattern classifier ⑥ classifies the encoded patterns and generates signals to control the control target ⑦.

Because such conventional technlogy uses binary codes or gray codes, such as shown in Table 1, for the encoding, in which it takes time to design the pattern there are cases in which complex pattern classifiers are required. This has been a problem standing in the way of reducing the size and cost, preventing the apparatus coming into widespread use as a myoelectric pattern interface.

TABLE 1

| Feature value | Gray code $X_1X_2X_3X_4$ | Binary code $X_1X_2X_3X_4$ |
|---|---|---|
| 0 | 0000 | 0000 |
| 1 | 0001 | 0001 |
| 2 | 0011 | 0010 |
| 3 | 0010 | 0011 |
| 4 | 0110 | 0100 |
| 5 | 0111 | 0101 |
| 6 | 0101 | 0110 |
| 7 | 0100 | 0111 |
| 8 | 1100 | 1000 |
| 9 | 1101 | 1001 |
| 10 | 1111 | 1010 |
| 11 | 1110 | 1011 |
| 12 | 1010 | 1100 |
| 13 | 1011 | 1101 |
| 14 | 1001 | 1110 |
| 15 | 1000 | 1111 |

In the case of binary code and gray code, involuntary changes in myoelectric patterns caused by changes in muscle tone can make it difficult to achieve correct pattern classification; accordingly, the range of applicability has been limited.

An object of the present invention is to resolve the above problems by providing a compact, low-price myoelectric-pattern classification method and apparatus that can be achieved by means of a simple processor and table-lookup apparatus.

Another object of the present invention is to provide a myoelectric-pattern classification method and apparatus that improve classification accuracy and promote the wider use of a myoelectric interface method and apparatus.

SUMMARY OF THE INVENTION

The myoelectric-pattern classification method of the present invention comprises using a group of surface electrodes on a skin surface to measure a myoelectric pattern that is ; an action potential generated by a coordinated action of a plurality of muscles, extracting a feature pattern from the measured myoelectric pattern, using redundant coding to encode the extracted feature pattern into a bit pattern, performing pattern classification on the encoded bit pattern and generating an output control signal.

Also, the myoelectric-pattern classification apparatus of the present invention comprises a group of surface electrodes that measures on a skin surface a myoelectric pattern that is an action potential generated by a coordinated action of a plurality of muscles, a feature-pattern extraction apparatus that extracts a feature pattern from the measured myoelectric pattern, an encoder that uses redundant coding to encode the extracted feature pattern into a bit pattern, and a pattern classifier that classifies the encoded bit pattern and generates an output control signal.

As described in the above, with the present invention in which redundant coding is used to encode feature patterns into bit patterns, with respect to arbitrary consecutive values the redundant code always differs by just one bit, differs by two bits when the difference is 2, and differs by three bits when the difference is 3, making it possible to realize a classification circuit with a simple circuit.

Other objects and features of the invention will be more apparent from the following detailed description of the invention based on the accompanying drawings.

DESCRIPTION OF THE PREFERRED EMBODIMENT

Figure 1:
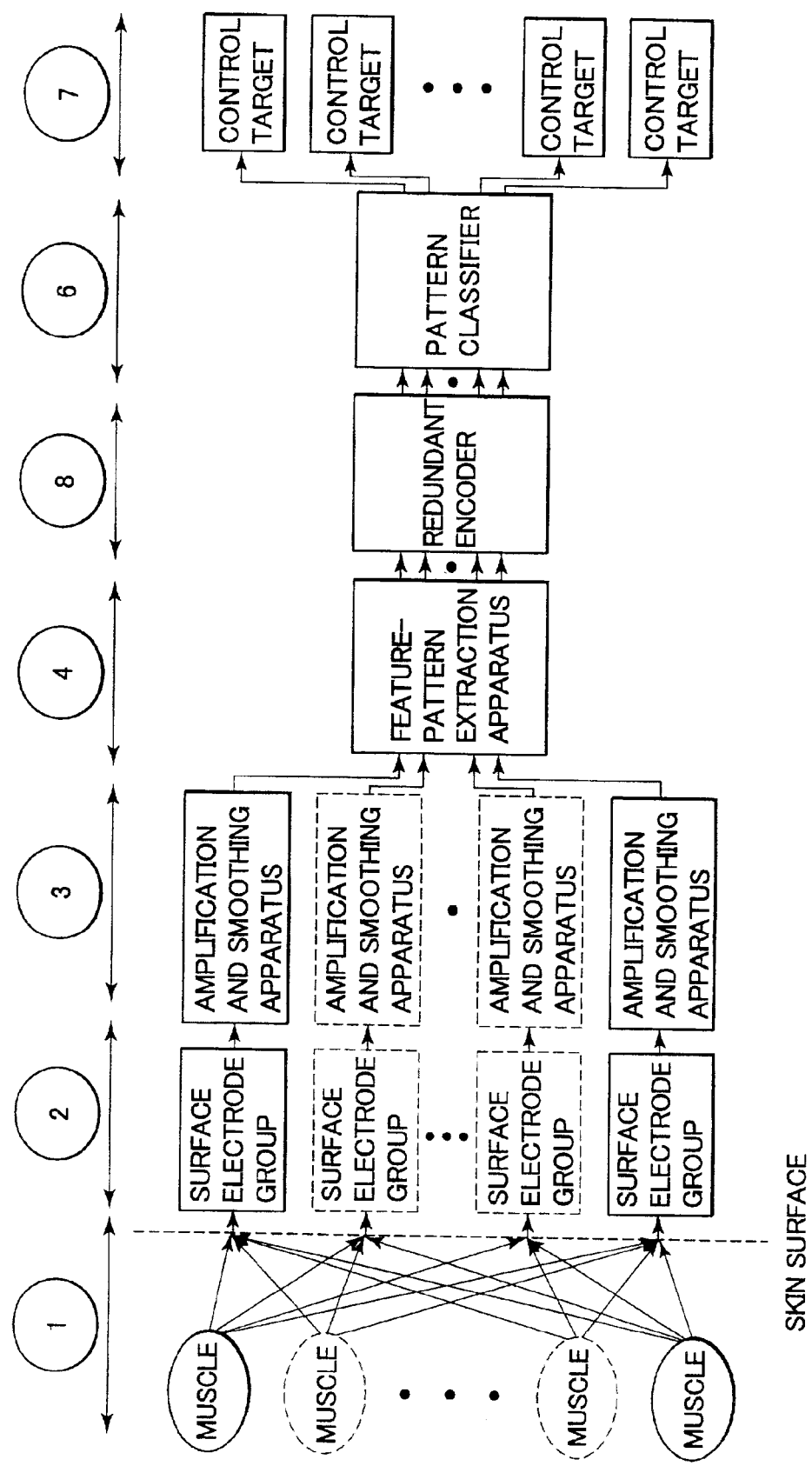
FIG. 1 is an explanatory drawing of the configuration of a myoelectric-pattern classification apparatus according to this invention.
Figure 2:
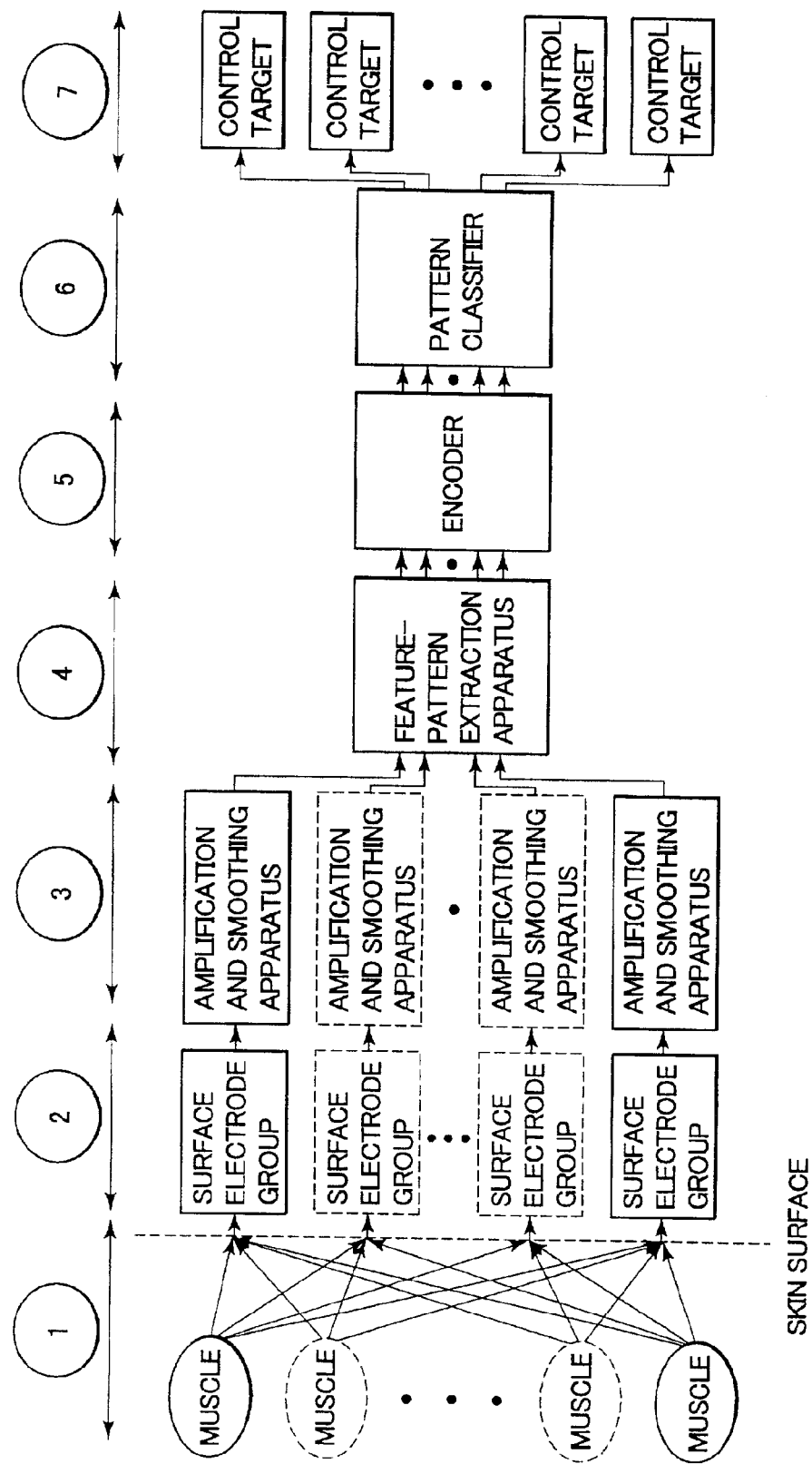
FIG. 2 is an explanatory drawing of the configuration of a myoelectric-pattern classification apparatus according to the prior art.

FIG. 1 shows a first example of a myoelectric-pattern classification apparatus that extracts a feature value from a myoelectric pattern and operates a control target, in which ① denotes myoelectric patterns, ② a surface electrode group, ③ amplification and smoothing apparatuses, ④ a feature-pattern extraction apparatus, ⑧ an encoder that uses redundant coding, ⑥ a pattern classifier, and ⑦ a control target such as a motor, a robot, a myoelectric arm prosthesis, and so forth.

As shown in the drawing, a myoelectric pattern ① that is an action potential generated by the coordinated action of a plurality of muscles is measured by one or a plurality of surface electrode groups ② on a skin surface. What is measured here is the sum of the action potentials generated by the plurality of muscles. Next, the measured potential is subjected to amplification and, when necessary, to smoothing by the amplification and smoothing apparatuses ③.

Feature patterns are extracted by the feature-pattern extraction apparatus ④. In the encoder ⑧, the extracted feature patterns are encoded into bit patterns, using the redundant code shown in Table 2. The pattern classifier ⑥ classifies the patterns encoded as bit patterns, and generates a signal to control the control object ⑦. A logical value filter, such as a logic circuit or the like, can be used as the pattern classifier.

TABLE 2

| Feature value | Redundant code $X_1X_2X_3X_4$ |
| --- | --- |
| 0 | 0000 |
| 1 | 0001 |
| 2 | 0011 |
| 3 | 0111 |
| 4 | 1111 |
| 5 | 1110 |
| 6 | 1100 |
| 7 | 1000 |

Below is an explanation of the myoelectric-pattern classification of the present invention applied to the action-decisions of a myoelectric arm prosthesis.

Figure 3:
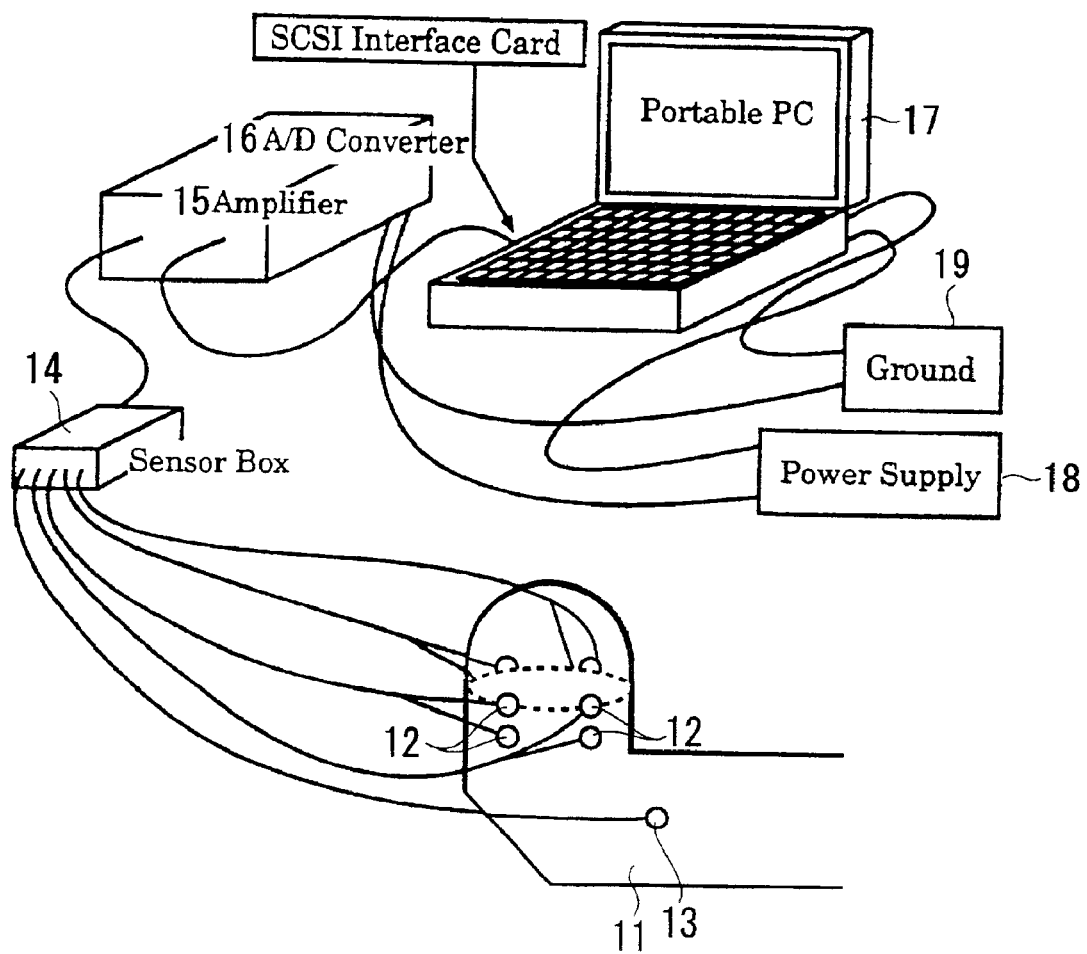
FIG. 3 is a general block diagram of an apparatus for measuring myoelectricity.

First, myoelectricity measurement will be described, using FIG. 3. Because the myoelectric signal is weak, in the order of several $\mu V$ to several mV, in the measurement thereof, it is generally necessary to subject a signal measured using two electrodes to differential amplification to reduce the effect of noise generated by power supplies or other electric devices. In this illustrated example, the myoelectricity measurement is made using eight (four sets) electrodes 12 applied to four locations around the forearm 11 of a myoelectric arm prosthesis. Reference numeral 13 denotes a reference electrode.

The weak myoelectric signals, measured by the four sets of electrodes 12, are sent, via a sensor box 14, to an amplifier 15 where they are differentially amplified and are then sent to an A/D converter 16. At the A/D converter 16, the amplified myoelectric signals are separated by 1000 Hz, converted into 12-bit digital signals and stored on a notebook type personal computer (PC) 17 connected by an SCSI interface. In the drawing, reference numeral 18 denotes a power supply and numeral 19 a ground. In this measurement, also, an analogue filter was used that blocks the commercial power supply frequency (50 Hz) in order to eliminate noise generated by the commercial power supply.

In the following explanation, equation 1 expresses a set of signals measured at time t.

$$f(t)=(f_1(t)f_2(t)f_3(t)f_4 \quad \text{[Equation 1]}$$

Myoelectricity measurements were carried out while the muscles were contracted as if to perform six actions (forearm pronation, forearmsupination, wrist flexion, wrist extension, hand closing and hand opening). That is, myoelectricity measurements were carried out while performing the muscle contractions shown in FIG. 4(*a*) (contracting the muscles after a two-second relaxation period and maintaining the contraction for three seconds) twenty times for each of the six actions (for a total of 120 times). In the case of forearm amputees, the myoelectricity measurements were carried out when the muscles were contracted based on a pre-amputation action image.

Figure 4:
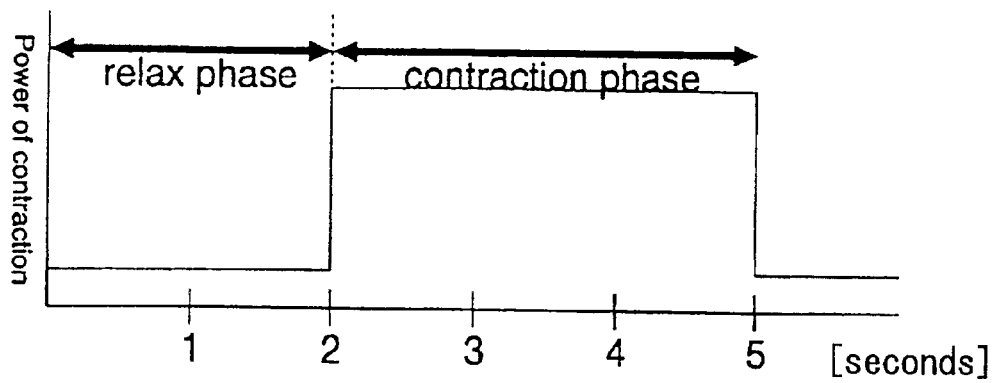
FIG. 4(a) is a graph showing the state of a muscle contracted for three seconds after being relaxed for two seconds.
FIG. 4(b) is a graph showing an example of a myoelectric signal during, in the state of FIG. 4(a), wrist flexion.
FIG. 4(c) is a graph showing an example of a myoelectric signal that is the myoelectric signal of FIG. 4(b) that has been subjected to smoothing processing.
Figure 4:
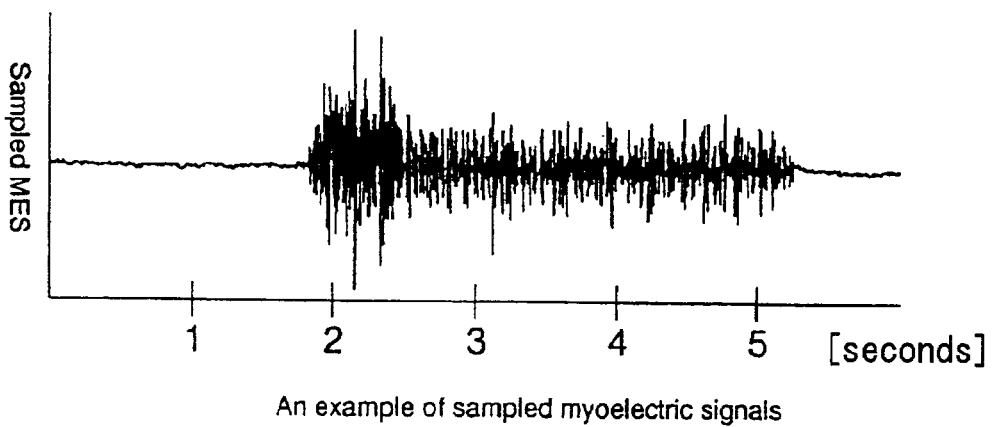
Figure 4:

FIG. 4(*b*) shows an example of myoelectricity measured on the surface of the skin over a flexed forearm muscle group during wrist flexion.

The measured myoelectric signals are subjected to smoothing processing to remove high-frequency components. Such smoothing processing is usually done with an analogue low-pass filter. However, in the case of these measurements, storage on the PC was effected without using a low-pass filter to avoid loss of information, so the smoothing processing was carried out on the PC. Specifically, a smoothed rectified value at time t is obtained by the calculation shown in equation 2. FIG. 4(*c*) shows an example of a smoothed rectified myoelectric signal.

$$g(t) = \left( \sum_{i=1}^{100} |f_1(t-i)|, \sum_{i=1}^{100} |f_2(t-i)|, \sum_{i=1}^{100} |f_3(t-i)|, \sum_{i=1}^{100} |f_4(t-i)| \right) \quad \text{[Equation 2]}$$

Myoelectric feature patterns used in action-decisions of an arm prosthesis are usually extracted using (1) a method in which the extraction is made from the myoelectricity measured at the time of the initiation of the muscle contraction, or (2) a method in which the extraction is made from the myoelectricicy measured during a state in which muscle contraction is maintained (hereinafter called the steady state). In the case of method (1), there is the advantage that the delay from the initiation of muscle contraction until the arm prosthesis starts an action is short. However, with respect to the action classification rate, method (2) is known to be better than method (1), so here, the feature patterns are extracted using steady-state myoelectricity.

The feature patterns are extracted using smoothed, rectified steady-state myoelectric values. This smoothing is also usually carried out using an analogue low-pass filter, but here, the average value of the values obtained on the PC by equation 2 during a period of one second is calculated and used as the feature pattern.

Figure 5:
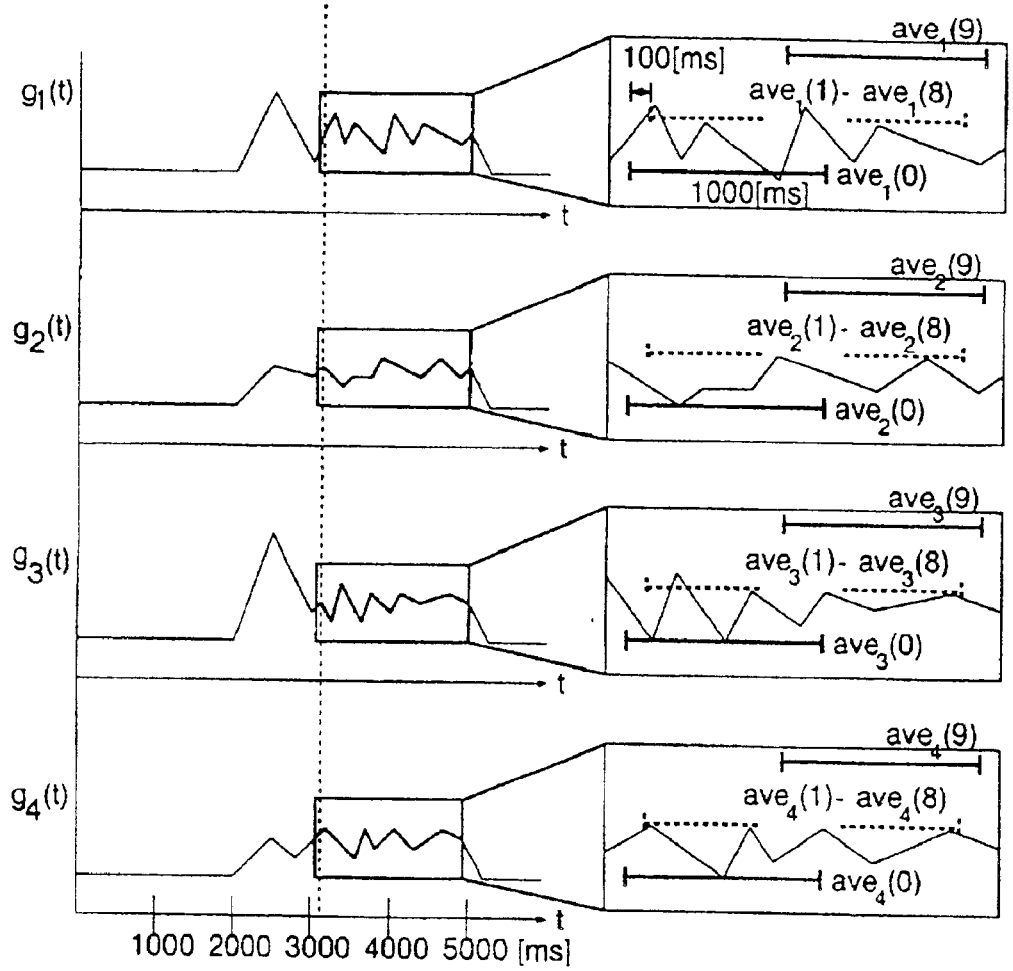
FIG. 5 is a drawing for explaining the feature-pattern extraction method.

In this feature-pattern extraction, in order to make it less tiring or the subject during the myoelectricity measurements ten averaged values for one muscle contraction are obtained. That is, as shown in FIG. 5, averaged values per second, each offset 100 milliseconds starting from one second after action initiation, are obtained using the calculation shown in equation 3. Here, reference symbol i denotes the time at which an action is initiated, that is, the time at which the value obtained by equation 4 exceeds a pre-set threshold value.

$$ave(n) = \frac{\sum_{j=1}^{1000} g(i+1000+j+n*100)}{1000} \quad (n = 0, 1, \ldots, 9) \quad \text{[Equation 3]}$$

$$G(t) = g_1(t) + g_2(t) + g_3(t) + g_4(t) \quad \text{[Equation 4]}$$

However, in practice, depending on how a muscle contracts, there are cases in which the value of equation 4 does not exceed the threshold value. Therefore, not all the twenty contractions per action can be used for the calculation of equation 3. Therefore, as training patterns for training the pattern classifier, equation 3 values are used from five of the muscle contractions in which the equation 4 value exceeded the threshold value (5 [muscle contractions]×10 [patterns]×6 [actions]=300 [patterns]). The equation 3 values extracted from another five muscle contractions are used as test patterns for evaluating the pattern classifier. In the following explanation, prepared training patterns are expressed by equation 5 and prepared test patterns are expressed by equation 6.

$$Tr_{org}(n) = (Tr_{org,1}(n), T_{rorg,2}(n), Tr_{org,3}(n), Tr_{org,4}(n)) \quad \text{[Equation 5]}$$

(n=0,1, ;299)

$$Te_{org}(n) = (Te_{org,1}(n), Te_{org,2}(n), Te_{org,3}(n), Te_{org,4}(n)) \quad \text{[Equation 6]}$$

(n=0,1, . . . ,299)

Figure 6:
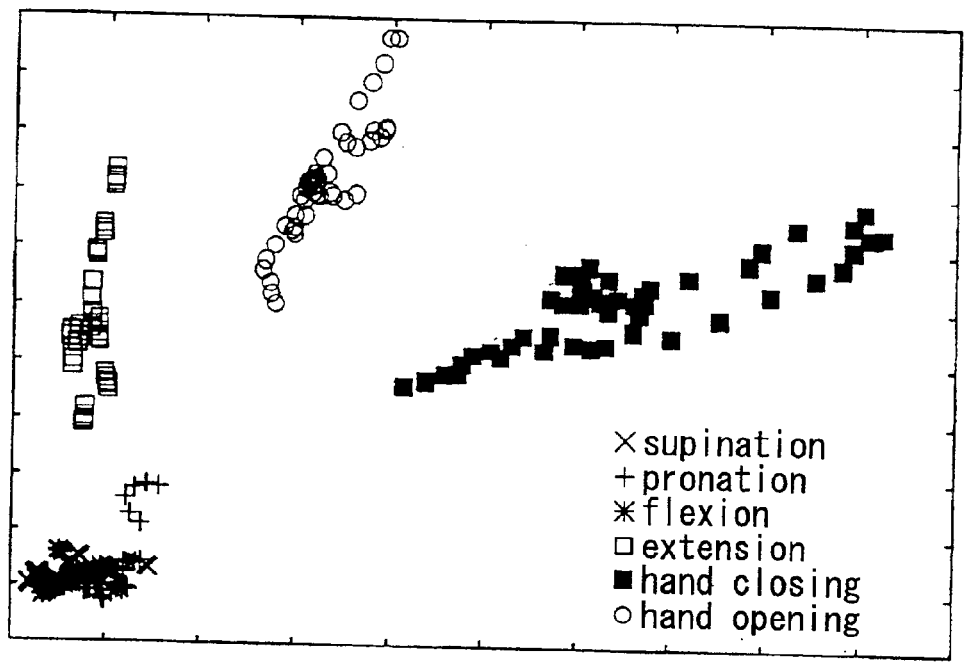
FIG. 6 is a diagram of the distribution of the myoelectric feature-pattern extraction method patterns.

FIG. 6 shows a plot, for each action, in which the first components of the above-described training patterns are X axis values and the second components are Y axis values.

The logarithmic transformation described in Japanese Patent Application No. 2001-020881 is also used here to extract feature patterns from the myoelectric patterns. Specifically, logarithmic transformation is carried out in accordance with the following equation 7 and equation 8.

$$Tr_{\log}(n) = (Tr_{\log,1}(n), Tr_{\log,2}(n), Tr_{\log,3}(n), Tr_{\log,4}(n)) \quad \text{[Equation 7]}$$
$$= (-\log(Tr_{org,1}(n)), -\log(Tr_{org,2}(n)), -\log(Tr_{org,3}(n)), -\log(Tr_{org,4}(n)))$$
$$(n = 0, 1, \ldots, 299)$$

$$Te_{\log}(n) = (Te_{\log,1}(n), Te_{\log,2}(n), Te_{\log,3}(n), Te_{\log,4}(n)) \quad \text{[Equation 8]}$$
$$= (-\log(Te_{org,1}(n)), -\log(Te_{org,2}(n)), -\log(Te_{org,3}(n)), -\log(Te_{org,4}(n)))$$
$$(n = 0, 1, \ldots, 299)$$

In the following, training patterns obtained with equation 5 and equation 7 are each used to train the pattern classifier, and test patterns obtained with equation 6 and equation 8 are used to evaluate the classifier. In the following, to simplify the explanation, the training pattern and test pattern are expressed by equation 9.

$$Tr = (Tr_1(n), Tr_2(n), Tr_3(n), Tr_4(n)), Te = (Te_1(n), Te_2(n), Te_3(n), Te_4(n)) \quad \text{[Equation 9]}$$

Here, a logic circuit is used to classify myoelectric patterns, so an evolvable chip is used as the pattern classifier employed in the classification. In contrast to conventional hardware where the circuit structure is fixed in the design process, the feature of this evolvable chip is that it is designed to adapt to specification changes or changes in the environment through its ability to reconfigure its circuit structure dynamically and autonomously.

An evolvable chip comprises hardware that can change the circuit configuration any number of times (reconfigurable hardware), and a circuit that adaptively changes the circuit configuration. The circuit configuration of this reconfigurable hardware can be changed any number of times by downloading a software bit-string called the configuration bit-string. A circuit that performs high-speed execution of a search technique called a genetic algorithm (hereinbelow abbreviated to GA) is used to adaptively rewrite the circuit configuration.

The GA is a search technique derived from the concept of biological evolution that carries out parallel searches for an optimum solution by encoding a plurality of candidate solutions in to bit-strings of 0 and 1. That is, the bit-strings are regarded as chromosomes and changes are effected through manipulations called crossings and mutations to thereby produce new candidate solutions. A pre-specified evaluation function is used to evaluate how close each chromosome (=candidate solution) is to a solution. Based on the results of these evaluations, solutions are sought by repeating the procedures to eliminate those that are far from the solution and leave those that are close to the solution.

In evolvable chips, the configuration bit-strings that specify the reconfigurable hardware circuit configurations are regarded as chromosomes. By applying a GA to evolve the chromosomes, if the evaluation functions are set appropriately it is possible to obtain a configuration bit-string that specifies the optimum circuit configuration.

The evolvable chip comprises (1) a GA operation circuit, (2) reconfigurable hardware, (3) memory for storing chromosomes (chromosome memory), (4) memory for storing training patterns (training-pattern memory), and (5) input/output interface.

Figure 7:
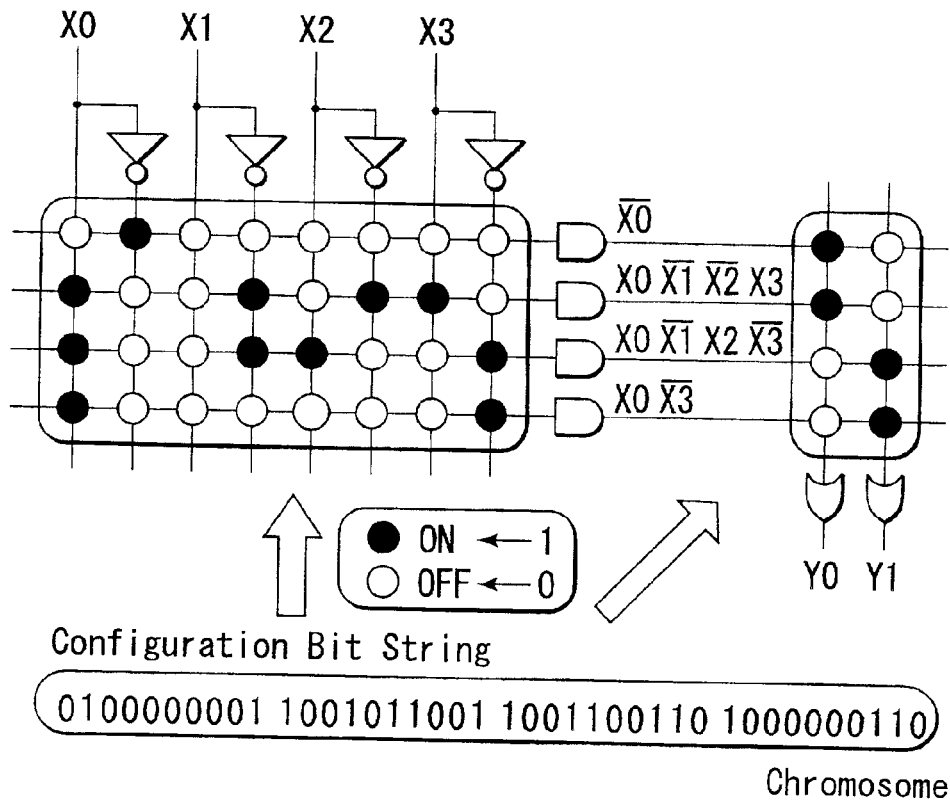
FIG. 7 is a diagram for explaining the structure of a Programmable Logic Array (PLA).

A Programmable Logic Array (hereinbelow abbreviated to PLA) is used for the reconfigurable hardware. As in the example shown in FIG. 7, the PLA comprises an AND array (producing the logical product of the connected input signals) and an OR array (producing the logical sum of the connected AND array output signals). In the diagram, the black bullets and white bullets indicate switches determining connections between inputs and outputs (black bullets signifying a connection). A logic circuit can be arbitrarily configured, using configuration bit-strings to specify the ON/OFF of a switch.

In pattern classification using the evolvable chip, in order to perform classification by means of the logic circuit, classification patterns have to be converted into bit-strings off 0 and 1. Here, the calculations of equation 10 and equation 11 are used to transform the myoelectric feature-patterns into real numbers from 0 to 15, which are transformed into integers that are coded as four-bit bit-strings.

$$sTr(n) = (sTr_1(n), sTr_2(n), sTr_3(n), sTr_4(n))$$
$$= 15 \times \left( \frac{Tr_1(n) - Tr_{1_{\min}}}{Tr_{1_{\max}} - Tr_{1_{\min}}}, \frac{Tr_2(n) - Tr_{2_{\min}}}{Tr_{2_{\max}} - Tr_{2_{\min}}}, \frac{Tr_3(n) - Tr_{3_{\min}}}{Tr_{3_{\max}} - Tr_{3_{\min}}}, \frac{Tr_4(n) - Tr_{4_{\min}}}{Tr_{4_{\max}} - Tr_{4_{\min}}} \right) \quad \text{[Equation 10]}$$

-continued $$(n = 0, 1\ldots, 299)$$

$(Tr_{1min}, Tr_{2min}, Tr_{3min}, Tr_{4min})$ : minimum value of $Tr_1(n), Tr_2(n), Tr_3(n), Tr_4(n)$ $(Tr_{1max}, Tr_{2max}, Tr_{3max}, Tr_{4max})$ : maximum value of $Tr_1(n), Tr_2(n), Tr_3(n), Tr_4(n)$ $$sTe(n) = (sTe_1(n), sTe_2(n), sTe_3(n), sTe_4(n))$$
$$= 15 \times \left( \frac{Te_1(n) - Tr_{1min}}{Tr_{1max} - Tr_{1min}}, \frac{Te_2(n) - Tr_{2min}}{Tr_{2max} - Tr_{2min}}, \frac{Te_3(n) - Tr_{3min}}{Tr_{3max} - Tr_{3min}}, \frac{Te_4(n) - Tr_{4min}}{Tr_{4max} - Tr_{4min}} \right)$$

[Equation 11]

$$(n = 0, 1\ldots, 299)$$

$(Tr_{1min}, Tr_{2min}, Tr_{3min}, Tr_{4min})$ : minimum value of $Tr_1(n), Tr_2(n), Tr_3(n), Tr_4(n)$ $(Tr_{1max}, Tr_{2max}, Tr_{3max}, Tr_{4max})$ : maximum value of $Tr_1(n), Tr_2(n), Tr_3(n), Tr_4(n)$ In the prior art, binary codes or gray codes, such as shown in Table 1, were used to code the bit-strings. However, using this encoding method has the following problems. As in the example shown in FIG. 6, myoelectric feature-patterns from each action distribute arbitrarily in a consecutive area.

This means that in order to use a logic circuit to classify the feature patterns, a circuit is required that outputs a 1 to arbitrary consecutive feature values. However, in the case of a gray code, a complex circuit maybe required to output a 1 to consecutive values. In the example shown below, the coded bit-string, that is, the circuit input signal, is expressed by equation 12.

$$X_1 X_2 X_3 X_4 \qquad \text{[Equation 12]}$$

For example, in cases where 1 is output to the consecutive sections 0 to 7, the 1 can be output to the values of the sections by the circuit expressed by equation 13.

$$\overline{X_1} \qquad \text{[Equation 13]}$$

However, in cases where 1 is output only to the consecutive sections 5 to 12, a circuit (equation 14) comprised of three product terms (logical product of input signals) is required. It is known that circuit synthesis using an evolvable chip takes time if the circuit to be synthesized comprises product terms of large input-signal numbers (for example: a product term of equation 12, or the product term (equation 15) or product term (equation 16) shown in the above examples comprised of four input signals or the like).

$$X_2 X_4 + X_2 \overline{X_3 X_4} + X_1 X_3 \overline{X_4} \qquad \text{[Equation 14]}$$

$$X_2 \overline{X_3 X_4} \qquad \text{[Equation 15]}$$

$$X_1 X_3 \overline{X_4} \qquad \text{[Equation 16]}$$

Thus, the time it cantake to synthesize the classification circuit 6 when gray code is used is one factor that can degrade the precision of the classification. In contrast, using the redundant code for the encoding makes it possible to realize the classification circuit with simple logic circuits, thus enabling the classification circuit to be synthesized at high speed by the evolvable chip, making it possible to improve classification precision.

Thus, when the formed training patterns were used to synthesize the evolvable chip circuits and the classification precision was evaluated using the training patterns, it was demonstrated that using the redundant code enabled the classification to be improved by an average of 3.1% for thirteen subjects, and by a maximum of 10.5%.

As for the time required for circuit synthesis, a comparison of the average value, for the thirteen subjects, of the number of circuit evaluations made using a training pattern showed that 451582.71 evaluations were needed when the redundant code was not used compared to 314333.91 when the redundant code was used. That is, it was reduced to 69.6% with the proposed technique.

The encoder 8 that characterizes the present invention uses the redundant code shown in Table 2 to encode feature patterns into bit patterns. This code is the code used as a Johnson counter output pattern, and as it is a redundant coding method, it can only code four-bit codes from 0 to 7.

A feature of this redundant code is the ability to output a 1 to an arbitrary consecutive value using just a simple circuit. That is, the code is designed so that when the difference between two values is 1 (section length of 2), the codes thereof will always differ by just one bit, and by two bits when the difference is 2, and by just three bits when the difference is 3.

For example, the redundant code for 1 is 0001 and the redundant code for 2 is 0011, which differ by only one bit. Also, the respective codes for 1 and 3 are 0001 and 0111, which differ by just two bits. Thus, to output a 1 to an arbitrary consecutive value of section length of 2 requires a circuit having a product term comprised of three input signals. For example, a 1 can be output to sections 1 to 2 by a circuit having the product term expressed by equation 17.

$$\overline{X_1 X_2} X_4 \qquad \text{[Equation 17]}$$

Similarly, using just a product term comprised of two input signals in the case of a section length of 3 and of one input signal in the case of a section length of 4, it is possible to realize a circuit that outputs a 1 to a value of those sections. And, in the case of a section length of 5 to 7, it can be realized by combining two of the product terms required in the case of a section length of 4.

For example, in the case of sections 1 to 6 (section length of 6), a circuit can be realized that outputs a 1 to a value of this section using the logical sum (equation 20) of a product term to output a 1 to sections 1 to 4 and a product term (equation 19) to output a 1 to sections 3 to 6.

$$X_4 \qquad \text{[Equation 18]}$$
$$X_2 \qquad \text{[Equation 19]}$$
$$X_2 + X_4 \qquad \text{[Equation 20]}$$

In this way, with the present invention, a classifier that classifies myoelectric patterns that distribute in consecutive areas can be achieved with a simple circuit.

Also, by using a redundant coding method, the present invention can be realized by means of a simple processor and table-lookup apparatus, making it possible to reduce the size and the cost.

This also makes it possible to increase the number of control objects that can be controlled, thereby making it possible to promote the wider use of myoelectric interface apparatuses.

What is claimed is:

1. A myoelectric-pattern classification method comprising using a group of surface electrodes on a skin surface to measure a myoelectric pattern that is an action potential generated by a coordinated action of a plurality of muscles, extracting a feature pattern from the measured myoelectric pattern, using redundant coding to encode the extracted feature pattern into a bit pattern, performing pattern classification on the encoded bit pattern and generating an output control signal.

2. A myoelectric-pattern classification apparatus comprising a group of surface electrodes that measures on a C. skin surface a myoelectric pattern that is an action potential generated by a coordinated action of a plurality of muscles, a feature-pattern extraction apparatus that extracts a feature pattern from the measured myoelectric pattern, an encoder that uses redundant coding to encode the extracted feature pattern into a bit pattern, and a pattern classifier that classifies the encoded bit pattern and generates an output control signal.

* * * * *